| United States Patent [19] | [11] Patent Number: 4,980,157 |
|---|---|
| Mercado et al. | [45] Date of Patent: Dec. 25, 1990 |

[54] COSMETIC IN FORM OF PRESSED POWDER

[75] Inventors: Clara Mercado, Aberdeen; Debra Verdon, Leonardo, both of N.J.

[73] Assignee: Revlon, Inc., New York, N.Y.

[21] Appl. No.: 453,098

[22] Filed: Dec. 13, 1989

Related U.S. Application Data

[63] Continuation of Ser. No. 883,676, Jul. 9, 1986, abandoned.

[51] Int. Cl.$^5$ .............................................. A61K 7/035
[52] U.S. Cl. ...................................... 424/69; 514/844
[58] Field of Search .................... 424/63, 69; 514/844

[56] References Cited

U.S. PATENT DOCUMENTS 4,137,302  1/1979  Humbert et al. ................. 424/61 X
4,650,672  3/1987  Yagita et al. .......................... 424/69

FOREIGN PATENT DOCUMENTS 0165137  10/1985  European Pat. Off. .............. 424/69
0110335   8/1979  Japan .................................... 424/69

*Primary Examiner*—John W. Rollins

[57] ABSTRACT

A pressed facial cosmetic powder is provided which is easily converted by scraping into loose powder form and includes a unique blend of different clays including kaolin and mica which imparts desired feel, compactability, moisture content, oil absorbability and platelet structure; the pressed powder includes in addition to the mixture of clays, dry binder, such as magnesium stearate, liquid binder, which may include lecithin, squalane, silicone, an ester and antioxidant, and colorants.

12 Claims, No Drawings

COSMETIC IN FORM OF PRESSED POWDER

This is a continuation of application Ser. No. 06/883,676 filed July 9, 1986, now abandoned.

FIELD OF THE INVENTION

The present invention relates to a pressed facial powder, hereinafter referred to as a "pressed powder" which is easily converted, by scraping the top layers thereof, into a loose powder ready for application.

BACKGROUND OF THE INVENTION

Facial makeup is normally applied in two steps. In a first step, liquid or cream foundation is applied. Next, a finishing powder is applied to complete the makeup.

Until now, the finishing powder has been available in the form of a loose dusty powder or as a pressed powder. The loose powder is preferred since it is easier to apply than the pressed powder; however, due to its fine particle size, the loose powder is very dusty and therefore essentially non-portable. Portable forms of finishing powder usually are in the form of pressed powders which include a talc filler, a dry binder such as calcium stearate, a liquid binder which includes an ester such as isopropyl myristate, squalane (Robane), isopropyl stearate, or isodecyl neopentanoate, an oil such as mineral oil or lanolin or mixtures thereof, as well as desired colorants.

Pressed powders have greater portability than loose powders. However, they are applied by a powder puff and in doing so, the powder puff must be pressed against the face of the pressed powder and take up powder to be applied. The difficulty arises in trying to take up adequate amounts of powder from the caked or pressed powder onto the powder puff. It has been found that if the same powder puff is employed too many times for such purpose, the powder puff may be impregnated with skin oils and thus will not lift powder from the pressed powder. Furthermore, constant contact of the powder puff with the upper layers of pressed powder causes the pressed powder to mat down and harden, thereby making it extremely difficult to lift off loose powder therefrom.

Thus, a pressed powder which is portable and non-dusting which may be easily converted to loose powder form would indeed represent an advance in the art and satisfy a long-felt want.

DESCRIPTION OF THE INVENTION

In accordance with the present invention, a pressed powder is provided which is portable but is easily converted to loose powder form by simply scraping or milling upper layers thereof with a mesh type strainer-like material. The loose powder so-produced therefrom is of desired texture and feel, will not plug-up the openings in such mesh material and is substantially dry but still creamy.

The pressed powder in accordance with the present invention includes a unique balance of clays which imparts to the pressed powder product desired moisture-content, oil absorption capacity and desired particle size and shape. In addition, the pressed powder of the invention will also contain one or more fillers, dry binders, liquid binders and colorants.

The unique balance of clays mentioned above will be formed of kaolin and mica in a ratio to each other of within the range of from about 1:1 to about 2:1 and preferably from about 1:1 to about 1.5:1. Such clays will impart sufficient moisture to the pressed powder of the invention so that it will remain in a creamy pressed or relatively congealed form but from which loose powder may be easily scraped therefrom. Thus, the clays will be present in an amount within the range of from about 20% to about 50% and preferably from about 30 to about 45% by weight of the pressed powder so as to impart a moisture content of from about 3 to about 6% and preferably from about 4 to about 5% by weight of the pressed powder.

The pressed powder will also include fillers in an amount within the range of from about 15 to about 70% and preferably from about 15 to about 30% by weight. Examples of such fillers include, but are not limited to, talc, rice starch (that is, pulverized grains from the rice plant, which also forms a soothing protective film) and/or bismuth oxychloride, with a mixture of rice starch and talc being preferred. In preferred embodiments, the fillers will comprise talc and rice starch employed in a weight ratio to each other within the range of from about 5:1 to about 20:1 and preferably from about 10:1 to about 15:1.

One or more dry binders will be present in an amount within the range of from about 3 to about 10% and preferably from about 3 to about 5% by weight of the pressed powder. Examples of suitable dry binders include but are not limited to magnesium stearate, zinc stearate, calcium stearate, lithium stearate and mixtures of two or more thereof, with calcium stearate being preferred.

The liquid binders will be present in an amount within the range of from about 2 to about 5% and preferably from about 2 to about 4% by weight of the pressed powder. The liquid binders are generally a mixture of bonding, lubricanting and moisturizing components and include, but are not limited to from about 2.7 to about 4.7% by weight (of the liquid binder) of squalane which is also referred to as Robane, a natural moisturizer that has been found to be a constituent of human sebum), from about 0.5 to about 1.5% by weight (of the liquid binder) of lecithin (which aids in forming a protectile coating of the skin), from about 0.1 to about 0.5% by weight (of the liquid binder), of one or more esters such as isopropyl myristate or isodecyl neopentanoate, from about 2 to about 3% by weight (of the liquid binder), of a silicone (which adds lubricity, reduces moisture loss without interfering with normal skin respiration), and mixtures thereof with a mixture of isopropyl myristate squalane, lecithin, and silicone being preferred.

The liquid binder may also include other ingredients such as one or more antioxidants, for example, Vitamin E tocopherol, in an amount within the range of from about 0.01 to about 0.03% and preferably from about 0.01 to about 0.02% by weight of the pressed powder.

Other ingredients which may be present in the pressed powder of the invention include one or more colorants, one or more preservatives in amounts of less than 1% by weight, such as methylparaben, propylparaben, imidazolidinyl urea, phenoxyethanol or mixtures thereof such as Phenonip and/or one or more fragrances.

Preferred formulations of the pressed powder of the invention are set out below:

| Ingredient | % by Weight of Pressed Powder |
| --- | --- |
| Clays | |
| Kaolin | 10 to 20 |
| Mica | 15 to 25 |
| Fillers | |
| Talc | 20 to 70 |
| Rice starch | 1 to 5 |
| Dry binder | |
| Calcium or magnesium stearate | 2 to 7 |
| Liquid binder | |
| Squalane | 0.5 to 1.5 |
| Lecithin | 0.1 to 0.5 |
| Silicone | 0.75 to 1.25 |
| Vitamin E tocopherol | 0.01 to 0.02 |
| Ester (isopropyl myristate) | 2 to 3 |

The pressed powder of the invention may be prepared by simply mixing the blend of clays, fillers, dry binders and colorants, micropulverizing the mixture so that is passes through a 0.013 inch screen and thus has an average particle size of from about 25 to about 35 microns, adding liquid binders, micropulverizing, if necessary, so that the mix passes through a 0.027 inch screen and thus has an average particle size of from about 40 to about 60 microns, and pressing the mixture in a mold, such as a compact, to form the pressed powder.

The pressed powder of the invention will preferably take the form of a creamy non-dusting finishing facial powder which is to be applied over liquid or cream foundation make-up. However, the pressed powder formulation of the invention may also be employed as an all over face color pressed powder including a face bronzer, eye shadow or blusher.

All of the above products are formulated as portable creamy pressed powders which may easily be converted into loose powder form by means of a scraper or scraping tool such as a mesh strainer material or other tool having a grating or rasp like surface. The pressed powder of the invention is formulated such that in loose powder form, it will have an average particle size of less than about 60 microns.

The following Example represents a preferred embodiment of the present invention.

EXAMPLE

A pressed finishing powder in accordance with the present invention having the following composition was prepared as described below.

| Ingredient | | | Parts by Weight |
| --- | --- | --- | --- |
| Kwangsi Talc #1 (filler) | | | 48 |
| Calcium stearate (dry binder) | | | 5 |
| Mica-M (clay filler) | | | 20 |
| Lion Kaolin (clay filler) | | | 15 |
| Methylparaben (Tegosept M) | } | preservatives | 0.1 |
| Imidazolidinyl urea (germall 115) | } | | 0.1 |
| Mibiron Brown | | | 3 |
| Mibiron Red | | | 0.5 |
| Mibiron Yellow | | | 1.1 |
| Mibiron Black | | | 0.2 |
| Rice starch (filler) | | | 2 |
| Robane binder intermediate | } | liquid binder | 4 |
| Silicone 225 | } | | 1 |
| Fragrance | | | 0.1 |
| | | | 100.1 |

| Robane Binder Intermediate | |
| --- | --- |
| Ingredient | Parts by Weight |
| Robane (Squalane) | 30 |
| Lecithin (Alcolec D.S.) | 5 |
| Vitamin E, NF-FCC (antioxidant) | 0.3 |
| Isopropyl myristate | 64.7 |
| | 100.0 |

The fillers and dry binder were mixed in a ribbon blender. The ingredients forming the liquid binder intermediate were mixed together with propeller mixing for 5 minutes until a homogeneous blend was formed.

The filler-dry binder was then micropulverized (0.013 inch screen, 30 to 40 microns) two times and returned to the ribbon blender and mixed. The liquid binder intermediate was then sprayed into the filler-dry binder mix in a fine mist and the mixtures blended until uniform. The mix was then passed through a micropulverizer (0.027 inch screen, 45 to 55 microns) and then blended again in the ribbon blender, then the mix was poured into a compact and pressed therein by means of a powder press, e.g., Cavalla, Kemwall or Vekico.

The product formed was a portable pressed powder which had a smooth creamy texture and feel and a moisture content of about 5% so that it remained in pressed solid form. However, the so-formed pressed powder was easily converted into loose powder by simply scraping upper layers thereof with a mesh or screen surface to form loose powder of proper particle size and texture, ready for use.

What is claimed is:

1. A pressed powder cosmetic composition that has a smooth creamy texture and feel while remaining in a creamy pressed or congealed form but which may be easily converted into loose powder form by simple scraping of the upper layer thereof, said composition consisting essentially of kaolin and mica, in a ratio between about 1:1 and about 2:1, said blend of clays supplying a moisture content of from about 3 to about 6% by weight of said composition, the blend of clays being present in an amount within the range of from about 20% to about 50% by weight of the pressed powder whereby said composition is convertible from said creamy pressed or congealed form to said loose powder form, a filler which is selected from the group consisting of talc, and rice starch, in a ratio of 5:1 to 20:1 and present in an amount within the range of from about 15 to about 70% by weight of the pressed powder, a dry binder selected from the group consisting of magnesium stearate, zinc stearate, calcium stearate, and lithium stearate present in an amount within the range of from about 3 to about 10% by weight of the pressed powder, and a liquid binder selected from the group consisting of the esters isopropyl myristate, and isodecyl neopentanoate; and squalane, lecithin or silicone present in an amount within the range of from about 2 to 5% by weight of the pressed powder wherein said liquid binder consists essentially of 2.7–4.7% squalane, 0.5–1.5% lecithin, 2–3% of an ester which is isopropyl myristate or isodecyl neopentanoate, and 2-3% silicone, all by weight of the pressed powder.

2. The composition as defined in claim 1 wherein said blend of clays is comprised of from about 10 to about 20% by weight kaolin and from about 15 to about 25 % by weight mica, by weight of said composition.

3. The composition as defined in claim 1 wherein the liquid binder is present in an amount within the range of from about 2 to about 4 % by weight of the pressed powder.

4. The composition as defined in claim 3 wherein the liquid binder further includes an antioxidant and isopropyl myristate or isodecyl neopentanoate.

5. The composition as defined in claim 4 wherein the antioxidant is Vitamin E tocopherol.

6. The composition as defined in claim 4 wherein the squalane is present in an amount within the range of from about 0.5 to about 1.5% by weight of the composition, lecithin is present in an amount within the range of from about 0.1 to about 0.2% by weight of the composition, silicone is present in an amount within the range of from 0.75 to about 1.25% by weight, and the ester is isopropyl myristate or isodecyl neopentanoate and is present in an amount within the range of from about 2 to about 3% by weight, all of said percentages being based on the weight of the pressed powder.

7. The composition as defined in claim 1 wherein said filler is present in an amount within the range of from about 15 to about 30% by weight of the pressed powder.

8. The composition as defined in claim 1 wherein the dry binder is present in an amount within the range of from about 3 to about 5% by weight of the pressed powder.

9. The composition as defined in claim 1 wherein the dry binder is comprised of calcium stearate, the liquid binder is comprised of squalane, lecithin, silicone and Vitamin E tocopherol and further including one or more colorants.

10. The composition according to claim 1 wherein the blend of kaolin and mica is present in a ratio of within the range of from about 1:1 to about 2:1.

11. The composition according to claim 10 wherein the ratio of kaolin to mica is within the range of from about 1:1 to about 1.5:1.

12. The composition of claim 1, wherein said ratio of kaolin to mica is between about 1:1 and about 1.5:1.

* * * * *